United States Patent [19]
Pruitt

[11] 4,080,693
[45] Mar. 28, 1978

[54] EMBALMING MACHINE FLOW CONTROL APPARATUS

[76] Inventor: Mike D. Pruitt, 213 E. Madison, McAlester, Okla. 74501

[21] Appl. No.: 752,871

[22] Filed: Dec. 20, 1976

[51] Int. Cl.² .............................................. A01N 1/00
[52] U.S. Cl. .................................................. 27/24 R
[58] Field of Search .................... 27/24 R, 21, 22 R; 128/230, 214 F, DIG. 12; 137/412; 32/33

[56] References Cited
U.S. PATENT DOCUMENTS

| | | | |
|---|---|---|---|
| 2,626,446 | 1/1953 | Moore | 27/24 R |
| 3,419,945 | 1/1969 | Sawyer | 27/24 R |
| 3,528,146 | 9/1970 | Markarian et al. | 27/24 R |

FOREIGN PATENT DOCUMENTS 565,011  11/1932  Germany ............................ 27/24 R

*Primary Examiner*—John D. Yasko
*Attorney, Agent, or Firm*—Dunlamp, Codding & McCarthy

[57] ABSTRACT

In combination with an injection needle disposed proximate to a working area and an embalming machine disposed remote from the working area, a flow control apparatus comprising a valve assembly having an inlet connected to the embalming fluid outlet of the embalming machine, an outlet connected to the injection needle and a valve movable between a closed position and an open position via a valve actuating assembly, the valve actuating assembly being responsive to control signals produced by a valve control unit disposed proximate to the working area.

5 Claims, 5 Drawing Figures

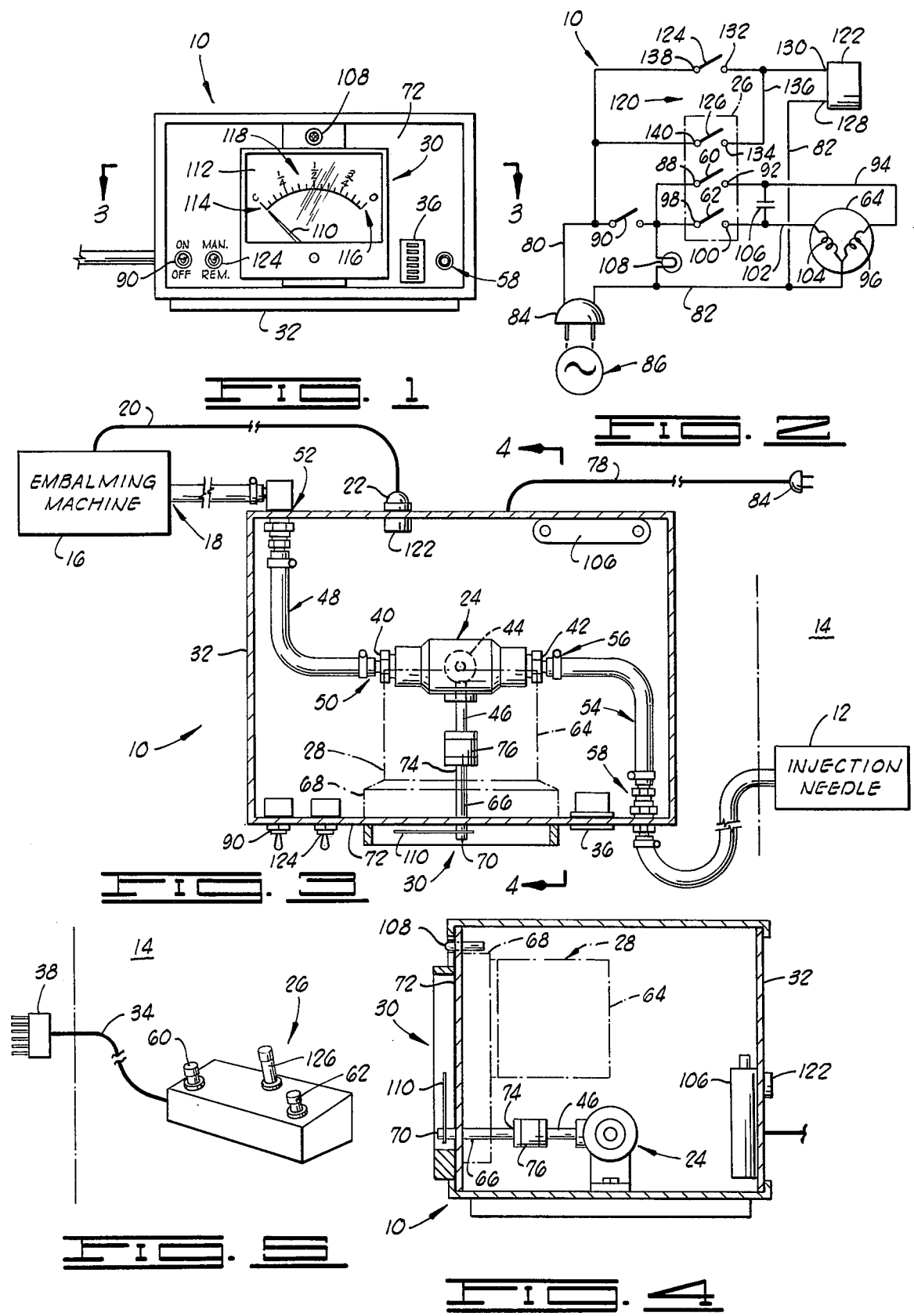

EMBALMING MACHINE FLOW CONTROL APPARATUS

BACKGROUND OF THE INVENTION

1. Field of the Invention

This invention relates generally to improvements in enbalming machine flow control and, more particularly, but not by way of limitation, to an embalming machine flow control apparatus having a valve assembly interposed between an embalming machine and an injection needle, with the position of the valve being controlled in response to control signals produced by a valve control unit disposed proximate to a working area.

2. Description of the Prior Art

It is well known to provide embalming machines with manually actuatable volume and pressure control valves, as can be seen in U.S. Pat. No. 3,419,945, issued to Sawyer, and U.S. Pat. No. 3,528,146, issued to Markarian et al. In addition, remotely actuatable motor valves are well known, as can be seen in U.S. Pat Nos. 1,832,809, issued to Hudson; 1,898,242, issued to Chandler; 3,248,080, issued to Plasko; 3,257,094, issued to Vischer Jr.; and 3,387,784, issued to Brenchley. It has also been proposed to provide such remotely actuatable motor valves with means for indicating the condition of the valve element, as can be seen in U.S. Pat Nos. 2,347,523, issued to Suksdorf; 2,451,989, issued to Smith; and 2,560,897, issued to Schmohl. However, it has not been proposed to interpose a motor valve between an embalming machine and an injection needle, a motor valve having an indicating apparatus providing an output indication of the position of the valve in conjunction with a valve control unit located proximate to a working area, such as the foot control units shown in U.S. Pat. Nos. 497,144, issued to Teal and 3,598,947, issued to Osborn.

SUMMARY OF THE INVENTION

In combination with an injection needle disposed proximate to a working area and an embalming machine disposed remote from the working area, a flow control apparatus comprising a valve assembly interposed between the embalming machine and the injection needle for varying the rate of flow of embalming fluid therebetween in response to control signals produced by a valve control unit disposed proximate to the working area.

An object of the present invention is to provide a flow control apparatus for varying the rate of flow of embalming fluid from an embalming machine disposed remote from a working area via a valve control unit disposed proximate to the working area.

Another object of the present invention is to provide a flow control apparatus providing a visual indication of the flow condition of a valve assembly which is responsive to a remote valve control unit.

Yet another object of the present invention is to provide a flow control apparatus having means facilitating the actuation thereof via an operator's foot.

Still another object of the present invention is to provide a simple and reliable flow control apparatus of the character described which is economical to manufacture and operate.

Other objects and advantages of the present invention will be evident from the following description when read in conjunction with the accompanying drawings which illustrate the preferred embodiment of the present invention.

BRIEF DESCRIPTION OF THE DRAWINGS

FIG. 1 is a plan view of a flow control apparatus constructed in accordance with the present invention.

FIG. 2 is a schematic diagram of the flow control apparatus of FIG. 1.

FIG. 3 is a cross-sectional view of the flow control apparatus of FIG. 1 taken along the line 3—3.

FIG. 4 is a cross-sectional view of the flow control apparatus of FIG. 1 taken along the line 4—4 of FIG. 3.

FIG. 5 is an isometric view of a valve control unit constructed in accordance with the present invention for use with the flow control apparatus of FIG. 1.

DESCRIPTION OF THE PREFERRED EMBODIMENT

Referring to the drawings in general and to FIGS. 2 and 3 in particular, shown therein and referred to by the general reference number 10 is a flow control apparatus constructed in accordance with the preferred embodiment of the present invention. The flow control apparatus 10 is constructed to operate in combination with a conventional injection needle 12 which is disposed proximate to a working area (indicated generally by the reference number 14), and an embalming machine 16 of well-known design disposed remote from the working area 14. In a conventional manner, the embalming machine 16 has an embalming fluid outlet 18 and a power cord 20 terminatng in a plug 22.

The flow control apparatus 10 is comprised primarily of a valve assembly 24, a valve control unit 26, a valve actuating assembly 28, and an indicator 30. In the preferred embodiment, the valve assembly 24, the valve actuating assembly 28, and the indicator 30 are mounted within a housing 32 disposed remote from the working area 14. In addition, the valve control unit 26 forms a separate unit disposed proximate to the working area 14. Preferably, the valve control unit 26 is connected to the various elements within the housing 32 via a cable 34 having a multi-terminal socket 36 and a cooperating multi-terminal plug 38 interposed therein.

The valve assembly 24 has an inlet 40, an outlet 42, and a valve 44 which is movable via a valve stem 46 between a closed position preventing fluid flow between the inlet 40 and the outlet 42, and an open position allowing fluid flow between the inlet 40 and the outlet 42. The valve assembly 24 may be of any desired conventional type, such as the ball valve commercially available from Nibco of Burkhart, Ind., as part number 400 WOG.

An inlet conduit 48 is connected between the embalming fluid outlet 18 of the embalming machine 16 and the inlet 40 of the valve assembly 24 in a conventional manner such as by the coupling apparatus indicated by reference numbers 50 and 52. An outlet conduit 54 is connected between the outlet 42 of the valve assembly 24 and the injection needle 12 in a conventional manner such as by the coupling apparatus indicated by reference numbers 56 and 58.

As can be seen most clearly in FIG. 5, the valve control unit 26 has a single-pole, single-throw open control switch 60 mounted thereon for producing an open control signal in response to the actuation thereof; and a single-pole, single-throw close control switch 62 mounted thereon for producing a close control signal in response to the actuation thereof. In the preferred embodiment, the valve control unit 26 is constructed in a convenient form to facilitate the actuation of the open control switch 60 and the close control switch 62 via the foot of the operator performing the particular embalming operation.

The valve actuating assembly 28 is connected to the valve assembly 24 and to the valve control unit 26 so that the valve actuating assembly 28 can receive the open control signal and the close control signal, with the valve actuating assembly 28 moving the valve 44 toward the open position in response to receiving the open control signal and moving the valve 44 toward the closed position in response to receiving the close control signal. More particularly, the valve actuating assembly 28 is comprised primarily of a reversible motor 64 which is coupled to an output shaft 66 via a reduction gear assembly 68. The output shaft 66 has a first end 70 extending through the front 72 of the housing 32, and a second end 74 coupled to the valve stem 46 via a coupler 76, such as that manufactured by Lovejoy Company, of Chicago, Ill., as part number L050. The valve actuating assembly 28 may be constructed in any convenient manner so as to provide a rate of rotation of the valve stem 46 on the order of four revolutions per minute. In particular, a valve actuating assembly 28 of suitable construction, including a motor 64 of the capacitor-start type, is manufactured by the Dayton Electric Manufacturing Company of Chicago, Ill., as model number 2Z813.

As can be seen most clearly in FIG. 2, the flow control apparatus 10 is provided with a power cord 78 consisting of a pair of conductors 80 and 82 which terminate in a plug 84 suitable for connecting the flow control apparatus 10 to an AC power source 86. The open control switch 60 has a pole terminal 88 connected to the conductor 80 via a single-pole, single-throw, on/off switch 90 mounted on the housing 32; and a throw terminal 92 connected via a conductor 94 to the conductor 82 through a forward winding 96 of the motor 64. The close control switch 62 has a pole terminal 98 connected to the conductor 80 via the on/off switch 90; and a throw terminal 100 connected via a conductor 102 to the conductor 82 through a reverse winding 104 of the motor 64. Since the motor 64 is of the capacitor-start type, a capacitor 106 is interposed between the conductors 94 and 102 in a conventional manner. If desired, a power indicator light 108 may be connected between the conductors 80 and 82, and mounted on the housing 32, to provide a perceivable output indication of the connection of the valve control unit 26 and the valve actuating assembly 28 to the AC power source 86.

The indicator assembly 30 is comprised primarily of a pointed 110 extending radially from the first end 70 of the output shaft 66 so as to be effectively connected to and movable with the valve 44, and a sector scale 112 (see FIG. 1) disposed on the front 72 of the housing 32 adjacent the pointer 110. Preferably, the scale 112 is provided with a closed gradation 114 corresponding to the position of the pointer 110 when the valve 44 is in the closed position, and an open gradation 116 corresponding to the position of the pointer 110 when the valve 44 is in the open position. As desired, other intermediate gradations, such as the ½ open gradation 118, may be provided on the scale 112.

Since it is frequently desirable to control the operation of the embalming machine 16 from the working area 14, the flow control apparatus 10 has also been provided with an embalming machine control assembly 120 for actuating the embalming machine 16 in response to the actuation thereof.

More particularly, the flow control apparatus 10 is provided with an outlet socket 122 mounted on the housing 32 for receiving the plug 22 of the embalming machine 16; a single-pole, single-throw manual/remote switch 124 mounted on the housing 32; and a single-pole, single-throw embalming machine control switch 126 disposed proximate to the working area 14. The outlet socket 122 has a first terminal 128 connected directly to the conductor 82, and a second terminal 130 connected to a throw terminal 132 of the remote/manual switch 124 and to a throw terminal 134 of the embalming machine control switch 126 via a conductor 136. The manual/remote switch 124 has a pole terminal 138 connected to the conductor 80, while the embalming machine control switch 126 also has a pole terminal 140 connected to the conductor 80. Preferably, the embalming machine control switch 126 is mounted on the valve control unit 26 to facilitate actuation thereof via the foot of the operator.

OPERATION OF THE PREFERRED EMBODIMENT

Prior to the operation of the flow control apparatus 10, the inlet 40 of the valve assembly 24 should be connected to the embalming fluid outlet 18 of the embalming machine 16 via the conduit 48, and the outlet 42 of the valve assembly 24 should be connected to the injection needle 12 via the conduit 54. In addition, the flow control apparatus 10 should be connected to the AC power source 86 via the plug 84, and the embalming machine 16 should be connected to the flow control apparatus 10 by inserting the plug 22 into the socket 122. Thereafter, the various controls of the embalming machine 16 may be adjusted to place the embalming machine 16 into a suitable condition for operation upon the actuation thereof.

If it is desired to actuate and deactuate the embalming machine 16 at selected times over the duration of a particular operation, the manual/remote switch 124 may be maintained in an open position so that the embalming machine control switch 126 forming a portion of the valve control unit 26 may be actuated by the operator to connect the embalming machine 16 to the AC power source 86 as desired. On the other hand, if it is desired to maintain the embalming machine 16 in an operating condition through the duration of the operation, the embalming machine 16 may be connected to the AC power source 86 by the closing of the manual/remote switch 124, thereby overriding operation of the embalming machine control switch 126.

Assuming hereinafter that the embalming machine 16 has been connected to the AC power source 86 via one of the switches 124 and 126, and that the valve assembly 24 has been actuated in a manner to be described via the valve actuating assembly 28 to place the valve 44 in the closed position, the operator may proceed to employ the injection needle 12 at the work area 14 in a conventional manner. When it is desired to initiate the flow of embalming fluid between the embalming machine 16 and the injection needle 112, the operator may initiate production of the open control signal by actuating the open control switch 60 via his foot. Thereafter, the valve actuating assembly 28 will respond to the open control signal by rotating the valve stem 46 via the output shaft 66 so as to move the valve 44 towards the open position. By observing the relationship between the pointer 110 and the scale 112, the operator may monitor the flow condition of the valve 44. Thus, when a desired flow rate through the valve assembly 24 has been achieved, the operator can terminate production of the open control signal by deactuating the open control switch 60.

As soon as the operator determines that it is desirable to lessen or terminate the flow of the embalming fluid, he may initiate production of the close signal by actuating the close control switch 62 via his foot. Alternatively, if the manual/remote switch 124 is in an open position, the operator may deactuate the embalming machine 16 via the embalming machine control switch 126. Assuming that the close control switch 62 has been actuated, the valve actuating assembly 28 will respond to the close control signal by rotating the valve stem 46 via the output shaft 66 so as to move the valve 44 towards the closed position. Again, the operator may observe the relationship between the pointer 110 and the scale 112 to monitor the flow condition of the valve 44 so as to maintain precise control of the flow of embalming fluid to the injection needle 12.

As will be clear to those skilled in the art, the flow control apparatus 10 as constructed in accordance with the preferred embodiment of the present invention greatly facilitates precise control of the flow of embalming fluid from an embalming machine 16 disposed remote from the working area 14 to an injection needle 12 disposed proximate to the working area 14. However, it is recognized that various changes may be made in the construction and the arrangement of the parts or the elements of the preferred embodiment as disclosed herein without departing from the spirit and the scope of the present invention as defined in the following claims.

What is claimed is:

1. In combination with an injection needle disposed proximate to a working area and an embalming machine disposed remote from the working area, the embalming machine having an embalming fluid outlet, a flow control apparatus comprising:
   a valve assembly having an inlet, an outlet and a valve movable between a closed position preventing fluid flow between the inlet and the outlet, and an open position allowing fluid flow between the inlet and the outlet;
   an inlet conduit connected between the embalming fluid outlet of the embalming machine and the inlet of the valve assembly;
   an outlet conduit connected between the outlet of the valve assembly and the injection needle;
   valve control means disposed proximate to the working area, the valve control means having an open control portion for producing an open control signal in response to the actuation thereof, and a close control portion for producing a close control signal in response to the actuation thereof;
   valve actuating means connected to the valve and to the valve control means, the valve actuating means receiving the open control signal and the close control signal, moving the valve toward the open position in response to receiving the open control signal, and moving the valve toward the closed position in response to receiving the close control signal; and
   indicating means connected to the valve for providing an output indication of the position of the valve relative to the open and closed positions.

2. The flow control apparatus of claim 1 further defined to include:
   embalming machine control means connected to the embalming machine, the embalming machine control means having an embalming machine control portion disposed proximate to the working area for actuating the embalming machine in response to the actuation thereof.

3. The flow control apparatus of claim 2 wherein the embalming machine control portion of the embalming machine control means is further characterized as being connected to the valve control unit.

4. The flow control apparatus of claim 2 wherein the embalming machine control means is further characterized as having a manual/remote portion disposed remote from the working area for actuating the embalming machine in response to the actuation thereof.

5. The flow control apparatus of claim 1 wherein the indicator apparatus is further defined to include:
   a pointer connected to and movable with the valve; and
   a scale disposed adjacent to the pointer, the scale having a closed gradation corresponding to the position of the pointer when the valve is in the closed position, and an open gradation corresponding to the position of the pointer when the valve is in the open position.

* * * * *